United States Patent [19]

Aoki et al.

[11] 4,082,661

[45] Apr. 4, 1978

[54] ACTIVATED CARBON AND PREPARATION THEREOF

[75] Inventors: Takao Aoki, Fuchu; Yuji Kako, Ichikawa; Toyoji Kikuga; Keizo Hatano, both of Fujieda, all of Japan

[73] Assignee: Sumitomo Durez Company, Ltd., Tokyo, Japan

[21] Appl. No.: 600,030

[22] Filed: Jul. 29, 1975

[30] Foreign Application Priority Data

Aug. 1, 1974 Japan .................................. 49-87553

[51] Int. Cl.$^2$ ............................................... B01D 15/00
[52] U.S. Cl. ................................ 210/40; 210/36; 252/421
[58] Field of Search ............... 210/496, 506, 39, 510, 210/500 R, 36, 40; 427/113, 114, 244, 384, 430; 252/421

[56] References Cited

U.S. PATENT DOCUMENTS

| | | | |
|---|---|---|---|
| 2,224,724 | 12/1940 | Elsey | 427/114 X |
| 2,595,290 | 5/1952 | Quinn | 210/39 X |
| 2,611,750 | 9/1952 | White | 210/510 |
| 2,978,350 | 4/1961 | Wilson | 427/230 |
| 3,251,724 | 5/1966 | Spokes et al. | 427/230 |
| 3,451,841 | 6/1969 | Kesten et al. | 427/244 X |
| 3,462,289 | 8/1969 | Rohl et al. | 427/294 |
| 3,753,500 | 8/1973 | Voegeli | 210/506 X |
| 3,825,460 | 7/1974 | Yoshikawa et al. | 252/421 X |

FOREIGN PATENT DOCUMENTS

| | | | |
|---|---|---|---|
| 2,141,606 | 7/1972 | Germany | 210/36 |
| 774,713 | 3/1957 | United Kingdom | 427/113 |

OTHER PUBLICATIONS

I. Goldstein, et al., "Stable Furfuryl Alcohol Impregnating Solution" 1969, pp. 57–58.

*Primary Examiner*—Charles N. Hart
*Assistant Examiner*—E. Rollins Cross
*Attorney, Agent, or Firm*—Peter F. Casella; James F. Mudd; William G. Gosz

[57] ABSTRACT

Activated carbon filtration materials are obtained by impregnating phenolic resins into inorganic porous bodies, such as ceramic filter tubes and plates, then baking the impregnated bodies to carbonize the resins. The invention also includes improved methods for purifying aqueous liquids contaminated with phenol, live bacilli, pyrogens, or water soluble organic dyes and a process for regenerating spent filters.

10 Claims, No Drawings

ACTIVATED CARBON AND PREPARATION THEREOF

BACKGROUND OF THE INVENTION

The present invention relates to compositions of activated carbon filtration materials which comprise active carbon composite materials obtained by impregnating inorganic porous bodies with phenolic resins then baking the impregnated bodies thereby carbonizing the resins, The object of the present invention is to provide activated carbon filtration materials of excellent active carbon sorptive characteristics capable of being in any shape such as pipe, plate or other optional figure for easy use and handling.

For filtration of fine particles or bacilli suspended in liquids, ceramic filter cylinders based on diatomaceous earths are used, and in the case of selective removal of a special solutes from liquids in chemical industry, food industry, pharmaceutical industry and so forth, activated carbon is generally used. However, for filtration and removal of alien substances from distilled water used as medium for medical injection fluid, alcholic drinks, refreshing drinks and other liquids which do not permit the presence of so-called "pyrogen" i.e., fever-generating substances, ceramic filter cylinders are inadequate. Thus physical filtration by specially made filter tubes having capillaries such as around 1 $\mu$ in radius or sorptive filtration by powdered activated carbon layers, individually or jointly, are employed for the removal. But as neither method is satisfactory there is at present an urgent need for developing more effective filtration materials.

When chemical raw materials and distilled water are processed to manufacture fluids for medical injection the latter are contaminated by various bacilli floating in the ambient air. In other words, there remain in such medical fluids, minute amounts of decomposed substances or bacilli corpses formed by metabolism not completely stopped. These substances are collectively denoted by the general term, "pyrogen," because they produce an extraordinary rise of the body temperature of warm-blooded animals on injection of the contaminated medical fluid. These pyrogens are generally considered to be endotoxins consisting mainly of cell wall phospholipid-polysaccharides of Gram-negative bacilli. Pyrogens are very heat-stable substances not readily destroyed by normal thermal sterilization. While they can be destroyed by a heat treatment of 30 minutes at 250° C, they can not be eliminated by conventional simple filtration methods because such substances have the common property of being easily soluble in water. Accordingly, the pharmaceutical industry is facing difficulties in eliminating them. At present, the industry is employing both high temperature treatment and long-term heat treatment with filtration by filter tubes having minute pores or with sorptive filtration through powdered activated carbon to remove these substances.

SUMMARY OF THE INVENTION

The present invention is based on the discovery that excellent activated carbon filtration materials are obtained by impregnating inorganic porous bodies such as conventional ceramic filter tubes or plates and the like, with thermosetting phenolic resins then drying and curing the resins and further baking and carbonizing such resin products in an inert atmosphere. The resultant novel products are very effective for the filtration of fine particles, bacilli or solutes and so forth dispersed in liquids for medical injection. It was also discovered that the sorptive ability of these products was remarkable enhanced by synergism between the physical filtration effect of the tube or plate and the chemical sorption effect of the activated carbon on the surfaces thereof, thereby providing activated carbon having possibilities of various shapes with improved absorptive power for the elimination of pyrogen.

The inorganic porous bodies which are the substrates in the present activated carbon filtration materials are natural or artificial inorganic porous bodies such as ceramics which have countless bended capillaries exemplified by filter tubes or cups, filter plates or spherical, cylindrical, or Raschig ring-form filtration materials generally in conventional use.

DETAILED DESCRIPTION OF THE INVENTION

Especially, for eliminating pyrogens, considering the amount of activated carbon fixed and its capacity in filtration, the apparent porosity of the inorganic porous bodies used as starting materials according to the invention should be more than 20%. It is desirable that the main distribution of capillary radii of the untreated substrate be within the range of 1,000A, and 70,000A, and that the capillary volume therein be within a range between 0.1 ml./g. and 0.5 ml./g., as determined by the mercury impregnating method. It is also desirable that the filter does not contain any water-soluble substance.

The phenolic resin for impregnating such inorganic porous bodies is selected to obtain the desired fixed amount of activated carbon and/or to obtain activated carbon of desired sorption characteristics. More particularly, the resin is a straight, i.e. unblended or unmodified phenol-formaldehyde resin, typically a one-step phenolic resin, i.e. a resole resin, including blends of resole resins with novolac resins. The phenolic resin can be derived from phenol, cresols, xylenols, etc. as the phenolic starting material. Such resins blended and/or modified with furan resins, urea resins, melamine resins, epoxy resins and the like can also be employed. The viscosity of the resin solutions employed for impregnation may vary according to the degree of condensation of the resin precondensate and the content of nonvolatile matter in the precondensate. Since degree of condensation in the resin prior to curing and viscosity of the resin solution are important factors in the permeation of the phenolic resin solution into the inorganic porous body and in the final distribution of activated carbon in the capillaries of the substrate body, it is first necessary to select an appropriate degree of condensation of the resin precondensate and subsequently to dilute the resin solution with an appropriate solvent or solvents so as to appropriately control the viscosity of the impregnating phenolic resin solution according to the state of distribution of pores in the particular substrate used.

If desired, the resin can be cured in the presence of an effective amount of an accelerator conventionally employed to harden such resins. In using accelerators for curing and fixing the resin precondensate, which is the main component of impregnating resin solutions, impregnation should be carried out by either impregnating the desired inorganic porous bodies with the resin solution previously mixed uniformly with curing accelerators just prior to impregnation, or by impregnating the substrate with such resin solutions after impregnating the curing accelerators into the capillaries of the inorganic porous substrate.

The impregnating process is carried out by first drying the inorganic porous substrate to eliminate the absorbed water therein. The dried substrate is then impregnated with the resin solution after evacuating the air inside the substrate capillaries. Depending on the nature of the substrate used, impregnation under elevated pressure may be necessary or desirable. Generally a desired proportion of fixed cured resin in the substrate can be attained by repetition of vacuum impregnation and heat curing.

At the end of the impregnating process, the excess resin solution adhering to the surface of inorganic porous bodies is eliminated by washing with a solvent or aqueous caustic soda solution. The impregnated bodies are then heated and the resin composition is cured under appropriate curing conditions. It is possible to cure the resin at ambient temperature by using a curing accelerator as mentioned above. However, in general, the impregnated body is heated to cure the resins at an elevated temperature controlled so as to prevent impregnated resin from being forced out of the capillaries of the substrate. The preferred curing temperature is between 160° and 180° C, and the heating time required to cure the resin is preferably from several hours to several tens of hours.

The inorganic porous bodies impregnated with phenolic resins in the foregoing manner are then subjected to a baking and carbonizing process. Naturally it is possible to simultaneously cure and bake such phenolic resin while carbonizing it, but, in order to provide a uniform distribution of carbonized carbon inside the capillaries of the substrate filtration materials, it is preferred to cure the phenolic resin uniformly, avoiding exuding the resin from the substrate.

The baking and carbonizing process is accomplished by heating the impregnated bodies at a temperature of above about 400° C in a non-oxidizing or reducing atmosphere or environment, such as a circulating steam or nitrogen gas, or a bed of particulate graphite or powdered coke and the like. If the baking temperature is too low, the ignition point of the activated carbon obtained in the inside of capillaries of the filtration material will be low and the sorptive capacity of the carbon will accordingly be undesirably small. If the baking temperature is too high, the volume of capillaries inside the filtration materials will be undesirably large, the ignition point of the carbon will be high, but the proportion of activated carbon deposibed in the substrate will be undesirably low. Accordingly, the baking and carbonizing temperature is desirably in the range between about 800° and 1,400° C.

The activated carbon filtration material obtained in such manner is of excellent heat and corrosion resistance, and its efficacy in filtering and eliminating bacilli of various kinds from liquid medicine is excellent due to the synergistic effects of physical filtration and chemical sorption, i.e., the substrate material has many capillaries and the activated carbon uniformly covers the surfaces thereof. In other words, the filtration quality and capacity is affected by the volume of capillaries and their distribution in the inorganic porous body and also by the quantity of activated carbon distributed in these capillaries. The quantity of the activated carbon deposited in the substrate is influenced by the carbonizing rate of phenolic resin which is further influenced by the kind of resin used, the quantity impregnated, the baking conditions and the like. If the carbonizing rate provides more than about 2 percent activated carbon (by weight), the product exhibits the sorption characteristics of an activated carbon. Activated carbon filtration materials of the invention with fixed activated carbon of more than about 2%, with the main distribution of capillary radii between 100A and 50,000A, and with capillary volume in the range between 0.05 and 0.50 ml./g. are useful in eliminating "pyrogen." However, activated carbon-containing materials having capillaries of larger radii or larger volumes are inferior in sorptive capacity and hence, are unsuitable for eliminating "pyrogen."

When the filtration capacity of the present activated carbon materials falls to an undesirable low level during use because of sorption of alien substances in the capillaries, it can be completely regenerated by baking in the aforementioned non-oxidizing or reducing atmosphere or environment, for example, in a nitrogen gas current, at a temperature between about 250° C and about 300° C without any damage to the carbon layer because of the high ignition point of the activated carbon of the present product. The activated carbon filtration materials obtained by the present invention can be put to practical use not only for eliminating "pyrogens" by filtration, but also for absorbing solvents or gases, eliminating various bacilli from brewery water; treating waste water to decrease the COD, ("Chemical Oxygen Demand," a measure of the oxygen equivalent of that portion of the organic matter in a sample that is susceptible to oxidation by a strong chemical oxidant as described in "Standard Methods for Examination of Water and Waste Water," American Public Health Association, Twelfth Ed. 1965, p. 510); BOD, ("Biological Oxygen Demand," the quantity of oxygen in parts per million which is utilized by aerobic biological organisms in the stabilization of decomposable organic matter during a stated time at a given temperature) etc.; as activated carbon sorption and filtration materials, as packing materials in gas dispersing towers, and as catalyst carriers and the like.

As mentioned above, the industrial usefulness of the activated carbon filtration product of the present invention is promoted by its ability to be manufactured in various shapes having a multiplicity of capillaries and excellent mechanical strength which can be adjusted as desired by selection of the inorganic porous substrate; and of the baking conditions for carbonizing the phenolic resin, thus combining physical filtration with chemical sorption properties. The present product is further characterized by its high sorptive capacity and its easy regeneration.

The following examples are presented to illustrate and explain more particularly the present invention, but the present invention is not restricted thereby. Parts, proportions and percentages in this specification and the following claims are by weight unless otherwise noted.

In the following Examples and Control the composition of the phenolic resins used were as follows:

Example 1 — Resole resin (caustic soda catalyst followed by neutralization with lactic acid), phenol/formaldehyde mole ratio = 1:1.3.

Example 2 — Resole resin (trimethylamine catalyst), phenol/formaldehyde mole ratio = 1:1.6.

Example 3 — as in Example 2.

Example 4 — 100 parts of solid resole resin (caustic soda catalyst), phenol/formaldehyde mole ratio = 1:1.6, and 40 parts of a proprietary furfural alcohol homopolymer precondensate (Durez 16470 resin).

Example 5 — as in Example 4.

Example 6 — Resole resin (caustic soda and ammonia catalysts), metacresol/formaldehyde mole ratio = 1:1.2.

Example 7 — Urea-melamine modified resole (caustic soda catalyst), urea/melamine/phenol/formaldehyde mole ratio = 0.515:0.016:0.469:2.5.

Example 8 — Melamine modified resole (caustic soda catalysts) melamine/phenol/formaldehyde = 0.725:0.275:2.71.

Example 9 — Epoxy blended resole: 100 parts of solid resole (ammonia and barium hydroxide catalysts, neutralized with lactic acid) and 5 parts of liquid proprietary epoxy resin (Den No. 431 resin).

Control — as in Example 2.

EXAMPLE 1

A cylindrical inorganic porous ceramic filter tube was dried for an hour at 110° C and then placed in a closed vessel. The vessel was maintained for an hour under a vacuum of −70cm Hg. Next an aqueous phenolic resin precondensate solution having a viscosity of 1.0 poise (25° C) and 65% (at 135° C) nonvolatile matter was poured into the vessel. The vessel was maintained at the latter vacuum for more than 1 hour. The inorganic porous filter tube was then removed from the vessel, and the excess resin solution on its surface was washed off with methanol. The resin of the impregnated tube was cured by placing the tube in a dryer and heating it from ambient temperature to 160° C over a period of about 8 hours.

In the cured product, the weight proportion of fixed phenolic resin based on the weight of filter tube was 19%, and after repeated impregnation with the phenolic resin and curing as described above, there was obtained a tube having a 25% proportion of fixed cured resin. The resin containing filter tube was placed in an activation furnace with a steam current, and the temperature of the furnace was raised to 900° C over a period of 6 hours. The tube was maintained for over one hour at 900° C, and was then cooled to ambient temperature within 12 hours, to activate the carbon. The proportion of activated carbon fixed in the filter tube as estimated by its heat loss in air for 4 hours at 800° C was 12%. No bacillus were found in the filtrate, obtained by filtering a test water sample containing 5 live bacilli per cubic centimeter, with the activated carbon filter tube. The tube was also effective in eliminating "pyrogen" since the body temperature elevation was 0.2° C after injection of the rats with the filtrate mentioned above compared with a temperature rise of 2.0° C after injection of the rats with the unfiltered test water.

The sorptive capacity of activated carbon in the pulverized powder of the present activated carbon filter tube as measured by testing its decoloring ability according to the methylene blue solution test method described in JIS K-1470-1967, "The Testing Methods of Powdered Active Carbon," was 150 milliliters per gram of powder, i.e., approximately the discoloring ability of commercially available powdered coconut shell active carbon, the sorptive capacity which is about 60 milliliters per gram.

EXAMPLES 2-5, and Control Example

Inorganic porous filter pipes with a size of 180 × 170 mm were heat-dried for an hour at 110° C and then placed in two closed vessels as described in Example 1. The vessels were maintained under a vacuum of −70 cm Hg. An aqueous phenolic resin precondensate solution having a viscosity of 2 poises (at 25° C) was charged to one vessel and a methanolic solution of a furan modified phenolic resin precondensate having a non-volatile matter intent of 70% (at 135° C) was poured into the other vessel. The pipes were impregnated respectively with each phenolic resin solution under the same vacuum for more than 1 hour. The inorganic porous filter tubes were then removed from the closed vessels, and excess resin solution on the surface was washed off with methanol. The tubes were then placed in a dryer and the temperature therein was raised from ambient to 160° C over a period of 8 hours, thereby curing the resin of the impregnated filter tubes.

In Examples 2 and 4 filter tubes containing the fixed phenolic resins were transferred to an activation furnace having a steam current flowing within and were then activated by raising the internal temperature of the furnace from ambient to 900° C over a period of 8 hours. The tubes were then maintained for more than 1 hour at the latter temperature. In Examples 3 and 5, the filter tubes were buried in steam-free graphite powder, and were baked in the reducing environment by raising the temperature from ambient to 1,000° C within 11 hours, thus carbonizing the fixed phenolic resins. The control Example samples were prepared by baking in graphite powder at a temperature of 800° C, (at a temperature 100° C lower than in the case of activating carbon with a steam current, but employing the same temperature elevation rate of 8 hours to 800° C).

In Table 1 the proportion of activated carbon fixed on the substrates, the results of the body heat generating test, (described in Table 1,) and the results of the aforementioned bacilli elemination test are presented for these examples.

TABLE 1

| | Example 2 | Example 3 | Example 4 | Example 5 | Control |
|---|---|---|---|---|---|
| Characteristics of Inorganic Porous Filter Tube: (1) Main Distribution of Radii of Capillaries (Angstroms) | 10,000–60,000 | 10,000–60,000 | 10,000–60,000 | 10,000–60,000 | 100–50,000 |
| (2) Volume of Capillaries (ml/g) | 0.12 | 0.12 | 0.12 | 0.12 | 0.60 |
| Resin Impregnated | phenolic resin | phenolic resin | furan modified phenolic resin | furan modified phenolic resin | phenolic resin |
| Proportion of Resin Fixed on Substrate (%) | 15 | 15 | 7 | 7 | 50 |
| Baking & Carbonizing | 900° C baked carbonized and | 1,000° C baked and | 900° C baked carbonized and | 1,000° C baked and | 800° C baked and |

TABLE 1-continued

| | Example 2 | Example 3 | Example 4 | Example 5 | Control |
|---|---|---|---|---|---|
| Conditions | steam activated | carbonized | steam activated | carbonized | carbonized |
| Proporton of Carbon (%) Fixed on Substrate | 4 | 6 | 2 | 3 | 30 |
| Body Heat Generating Test* (° C) | 0.00–0.25 | 0.00–0.55 | 0.00–1.00 | 0.05–0.70 | 0.30–1.65 |
| Effectiveness in Elimination of Pyrogen | Successful | Successful | Successful | Successful | Failed |

(Note)
*The Heat Generating Test was carried out by injecting the aqueous filtrate obtained from the activated carbon filter tubes into rats and measuring the body temperature rise over a period of 3 hours. In the above reported data, the two figures separated by a hyphen represent the minimum and maximum, respectively in 9 rat tests. As control there was used unfiltered liquid containing pyrogen for which the comparable Body Heat Generating Test data was 1.40–2.20° C., minimum and maximum respectively.

In the above Table 1 all figures in the first horizontal line represent the main distribution of capillary radii in the untreated porous inorganic bodies.

Despite use in the control of an inorganic porous body having a smaller main distribution of capillary radii than the substrates of the test Examples 2–5, despite greater fixation of resin and carbon for overcoming the larger capillary radii in the control as compared to the test substrates and despite use of a somewhat lower baking and carbonizing temperature in preparing the control product, the control product proved ineffective in removing pyrogen.

EXAMPLES 6–9

Inorganic porous filter plates having a main distribution of capillary radii of 100 – 50,000A and a capillary volume of 0.60 millilitre per gram were vacuum treated as described in Example 1, then impregnated with phenolic resin solutions respectively. The inorganic porous filter plates were removed from the impregnating bath, and after their surfaces had been washed free of excess resin solution with methanol, they were placed into a dryer, the temperature of which was raised from ambient to 160° C over a period of 4 hours. The plates were buried in graphite powder, and resin baked in the reducing environment to carbonize the phenolic resins, the temperature being raised to 800° C over a period of 8 hours. The properties of the activated carbon filter plates obtained are presented in Table 2. All samples are characterized as containing carbon in active form.

TABLE 2

| | Ex. 6 | Ex. 7 | Ex. 8 | Ex. 9 |
|---|---|---|---|---|
| Resin Impregnated | cresol resin | urea-melamine modified phenolic resin | melamine-modified phenolic resin | epoxy-modified phenolic resin |
| Solvent | methanol-acetone | water | methanol | methyl ethyl ketone |
| Viscosity (poises/25° C) | 0.6 | 5.0 | 0.5 | 5.0 |
| Non-Volatile Matter (%,135° C) | 60 | 75 | 60 | 65 |
| Fixed Resin (%) | 55 | 29 | 54 | 25 |
| Fixed Carbon (%) | 32 | 10 | 20 | 13 |
| Discoloring Ability of Methylene Blue (JIS K-1470) (ml./g) | 210 | 180 | 180 | 160 |

Waste water contaminated with phenol was treated with the activated carbon filter plates to test their sorptive capacity in removing the phenol impurity. The phenol content of the waste water was decreased from about 100 ppm to about 0.5 ppm on treatment with the plates. The sorptive capacity of the treated plates was greater than about 140 milligrams of phenol per gram of activated carbon in the plates. The sorptive capacity of the spent activated carbon-containing filter plates was regenerated by baking the spent plates at 400° C in a reducing environment.

The untreated porous inorganic plates used as starting material in the above examples were ineffective in discoloring and sorptive operations.

In Examples 4,5, and 7 above the resins may also be cured in the presence of a small effective amount of a cure accelerator such as p-toluene sulfonic acid, conveniently charged as a 50% aqueous solution, or hydrochloric acid, conveniently 37% aqueous hydrochlorid acid. Typically about 1 to 2% of accelerator based on the weight of resin is used.

It is to be understood that the invention is not limited to the specific examples which have been offered merely as illustrative of the invention and that modifications can be made therein without departing from the spirit of the invention.

What is claimed is:

1. A method of preparing an activated carbon-containing inorganic porous shaped article capable of filtration of aqueous liquids which comprises impregnating an inorganic porous article which is substantially free of water-soluble substances and absorbed moisture and has a main capillary radii distribution between about 1000 and about 70,000 Angstrom units and an average capillary volume between about 0.1 ml./g. and about 0.5 ml/g. with a curable phenolic resin, curing said phenolic resin therein and subsequently baking said cured resin-impregnated article at a temperature above about 400° C in a non-oxidizing environment to provide at least about 2 weight percent activated carbon in said article, said activated carbon-containing article having a main capillary radii distribution between about 100 and about 50,000 Angstrom units and an average capillary volume between about 0.05 ml./g. and about 0.5 ml./g.

2. The method of claim 1 wherein the porous shaped article is a ceramic tube, cup, plate, cylinder sphere or ring; the phenolic resin is a phenol-formaldehyde resin, a furan-blended or modified phenol-formaldehyde resin, a urea blended or modified phenol-formaldehyde resin, a melamine-blended or modified phenol-formaldehyde resin or an epoxy resin blended or modified phenol-formaldehyde resin; the curing is accomplished at a temperature between about 160° and about 180° C; the amount of cured resin fixed in the article is about 5 to about 55 percent based on the weight of the impregnated article.

3. The method of claim 2 wherein the baking temperature is about 800° to about 1400° C, and the non-oxidizing environment for baking is selected from the group consisting of steam, nitrogen gas, particulate graphite, powdered coke and mixtures thereof.

4. The method of claim 3 wherein the phenolic resin is a resole and the amount of activated carbon fixed in the article after baking is about 3 to 32 percent based on weight of the baked article.

5. The method of claim 4 wherein the article is impregnated with the phenolic resin dissolved in a solvent selected from the group consisting of water, methanol, methyl ethyl ketone, acetone and mixtures thereof under diminished pressure, excess resin is removed from the surface of said impregnated article by washing the article with said solvent or aqueous caustic soda and the solvent or water is removed by evaporation prior to curing.

6. The method of claim 5 wherein the phenol of the phenolic resin is selected from the group consisting of phenol and meta-cresol.

7. In the process of purifying aqueous liquids contaminated with impurities selected from the group consisting of phenol, live bacilli, pyrogen, and water-soluble organic dyestuffs, which comprises filtering the contaminated liquid with an inorganic filter and contacting the contaminated liquid with activated carbon, the improvement which comprises employing as said filter and activated carbon an inorganic porous article impregnated with a non-oxidatively carbonized cured phenolic resin, said filter containing at least about 2 percent by weight activated carbon and having a main capillary radii distribution between about 100 and 50,000 Angstrom units, and an average capillary volume between about 0.05 ml./g. and about 0.5 ml./g.

8. An activated carbon-containing porous inorganic article prepared by the process of claim 1.

9. An activated carbon-containing porous inorganic article prepared by the porous of claim 6.

10. A method for generating the sorptive capability of a spent filter comprising an inorganic porous article having a main pore radii distribution between about 100 and about 70,000 Angstrom units and an average pore volume between about 0.05 ml/g and about 0.5 ml/g, impregnated with a non-oxidatively carbonized, cured phenolic resin and containing at least 2 weight percent activated carbon, said filter being satiated in sorptive capacity with a member of the group consisting of phenol, live bacilli, pyrogen and water-soluble organic dyestuff sorbed therein, which comprises baking said spent filter at a temperature of about 250° to about 400° C in a non-oxidizing environment whereby the sorptive capacity of the filter is regenerated without substantial damage to the activated carbon.

* * * * *